(12) United States Patent
Dohi

(10) Patent No.: US 11,188,736 B2
(45) Date of Patent: Nov. 30, 2021

(54) OBSERVATION DEVICE

(71) Applicant: OLYMPUS CORPORATION, Tokyo (JP)

(72) Inventor: Masahito Dohi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/025,372

(22) Filed: Sep. 18, 2020

(65) Prior Publication Data

US 2021/0027043 A1    Jan. 28, 2021

Related U.S. Application Data

(63) Continuation of application No. PCT/JP2019/012043, filed on Mar. 22, 2019.

(30) Foreign Application Priority Data

Mar. 30, 2018 (JP) .............................. JP2018-066393

(51) Int. Cl.
| | |
|---|---|
| *G06K 9/00* | (2006.01) |
| *C12M 1/00* | (2006.01) |
| *C12M 1/34* | (2006.01) |
| *G01N 15/06* | (2006.01) |
| *G02B 23/24* | (2006.01) |

(Continued)

(52) U.S. Cl.
CPC ......... *G06K 9/00134* (2013.01); *C12M 31/02* (2013.01); *C12M 41/36* (2013.01); *G01N 15/06* (2013.01); *G02B 23/2469* (2013.01); *G02B 23/2484* (2013.01); *H04N 5/2256* (2013.01);

(Continued)

(58) Field of Classification Search
None
See application file for complete search history.

(56) References Cited

U.S. PATENT DOCUMENTS

| | | |
|---|---|---|
| 2014/0003858 A1 | 1/2014 | Frazier |
| 2014/0284460 A1 | 9/2014 | Nishimura |

(Continued)

FOREIGN PATENT DOCUMENTS

| | | |
|---|---|---|
| EP | 2 796 084 A1 | 10/2014 |
| EP | 3 085 296 A1 | 10/2016 |

(Continued)

OTHER PUBLICATIONS

International Search Report dated Jun. 25, 2019 received in PCT/JP2019/012043.

*Primary Examiner* — James M Anderson, II
(74) *Attorney, Agent, or Firm* — Scully, Scott, Murphy & Presser, P.C.

(57) ABSTRACT

An observation device includes: an illumination unit that generates illumination light to be radiated onto cells floating in a culture fluid inside a culture vessel; a light receiving unit that receives observation light coming from the cells that have been irradiated with the illumination light, the observation light being imaged by an image-forming optical system; and a casing that has a transmissive section so as to transmit the illumination light and the observation light and that accommodates the illumination unit and the light receiving unit, wherein the casing has an elongated cylindrical form that is configured to be inserted into the culture fluid via a port used to insert a tube into the culture vessel.

13 Claims, 15 Drawing Sheets

(51) Int. Cl.
    *H04N 5/225*    (2006.01)
    *G01N 15/00*    (2006.01)
(52) U.S. Cl.
    CPC ............... *G01N 2015/0065* (2013.01); *G01N 2015/0693* (2013.01)

(56) References Cited

U.S. PATENT DOCUMENTS

| | | |
|---|---|---|
| 2014/0377848 A1 | 12/2014 | Zink et al. |
| 2016/0291313 A1 | 10/2016 | Tojo et al. |
| 2018/0155667 A1 | 6/2018 | Stobbe |
| 2019/0161724 A1* | 5/2019 | Kang .................... C12M 31/06 |

FOREIGN PATENT DOCUMENTS

| | | |
|---|---|---|
| JP | 3823120 B1 | 9/2006 |
| JP | 2007-156191 A1 | 6/2007 |
| JP | 2013-146535 A1 | 8/2013 |
| JP | 2014-518076 A | 7/2014 |
| JP | 5866006 B2 | 2/2016 |
| JP | 2017-140006 A | 8/2017 |
| WO | 2013/183121 A1 | 12/2013 |
| WO | 2015/093278 A1 | 6/2015 |
| WO | 2017/025210 A1 | 2/2017 |
| WO | 2018/168983 A1 | 9/2018 |

* cited by examiner

Time 1

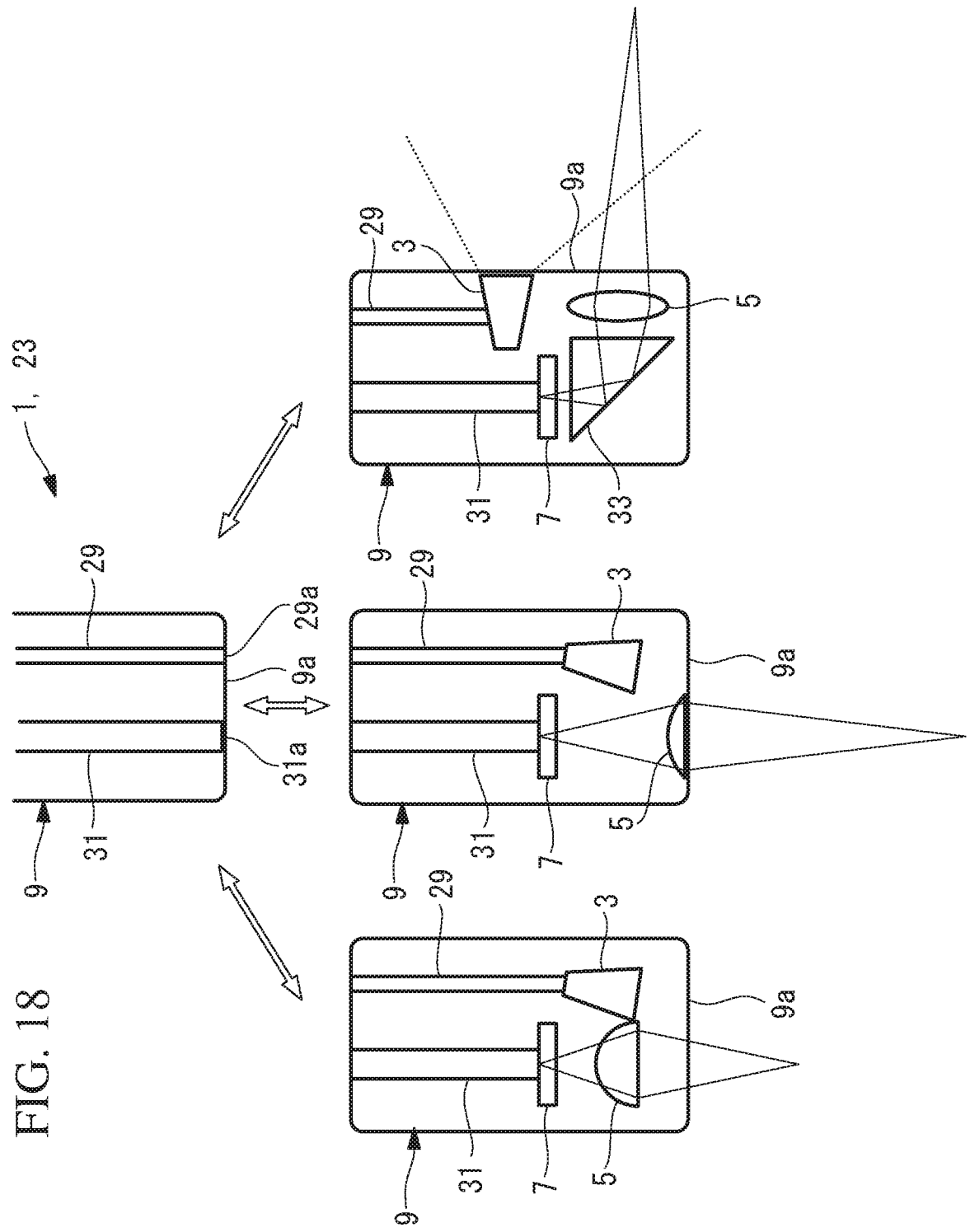

//(1)
OBSERVATION DEVICE

CROSS-REFERENCE TO RELATED APPLICATIONS

This is a continuation of International Application PCT/JP2019/012043 which is hereby incorporated by reference herein in its entirety.

This application claims the benefit of Japanese Patent Application No. 2018-066393, the content of which is incorporated herein by reference.

TECHNICAL FIELD

The present invention relates to an observation device.

BACKGROUND Art

In the field of regenerative medicine, including the field of ips cells (induced pluripotent stem cells), scaling-up of cell culturing is desired. For the mass production of cells, the culturing is changing from conventional adherent culturing using a vessel called a well plate or dish to culturing using a suspension culturing vessel called a bioreactor. In culturing using a suspension culturing vessel, cells are cultured in a state in which the cells are made to float in a liquid by stirring the liquid inside the suspension culturing vessel.

As a method for observing cells using a suspension culture vessel, there is a known method described in PTL 1, for example. In the method described in PTL 1, an image of cells floating in a liquid inside a suspension culture vessel is acquired by means of an illumination device and an image acquisition device that are disposed outside the suspension culture vessel. The particle-size distribution of cells and the total number of cells are calculated through arithmetic processing using image analysis and parameters input in advance.

CITATION LIST

Patent Literature

{PTL 1} Japanese Unexamined Patent Application, Publication No. 2017-140006

SUMMARY OF INVENTION

According to one aspect, the present invention provides an observation device for observing cells floating in a culture fluid inside a culture vessel, the observation device including: an illumination unit that generates illumination light to be radiated onto the cells; a light receiving unit that receives observation light coming from the cells that have been irradiated with the illumination light, the observation light being imaged by an image-forming optical system; and a casing that has a transmissive section so as to transmit the illumination light and the observation light and that accommodates the illumination unit and the light receiving unit, wherein the casing has an elongated cylindrical form that is configured to be inserted into the culture fluid via a port used to insert a tube into the culture vessel.

BRIEF DESCRIPTION OF DRAWINGS

FIG. 18 is a longitudinal sectional view of the casing, showing three example replaceable configurations of the image-forming optical system according to a modification of the first embodiment and the second embodiment of the present invention.

DESCRIPTION OF EMBODIMENTS

First Embodiment

An observation device according to a first embodiment of the present invention will be described below with reference to the drawings.

Figure 1:
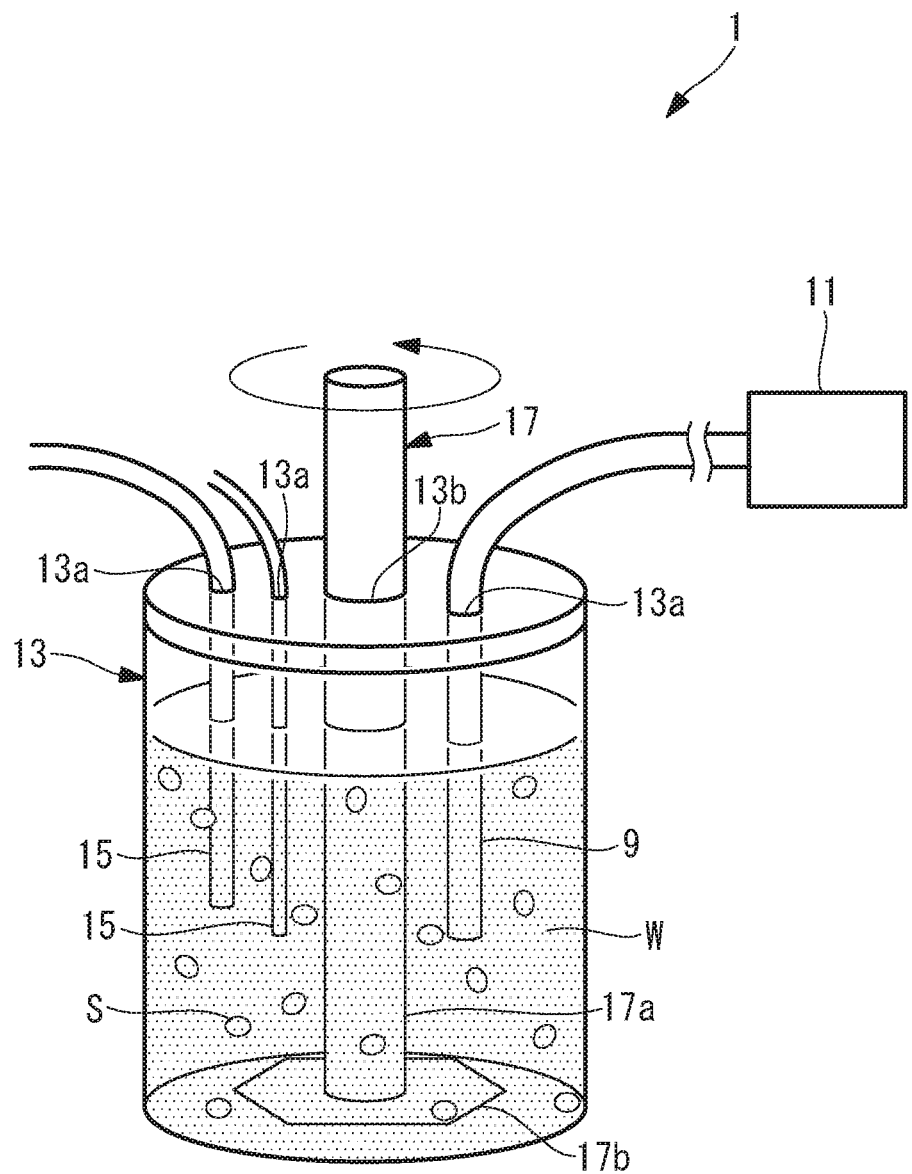
FIG. 1 is a schematic configuration view showing an observation device and a culture vessel according to a first embodiment of the present invention.
Figure 3:
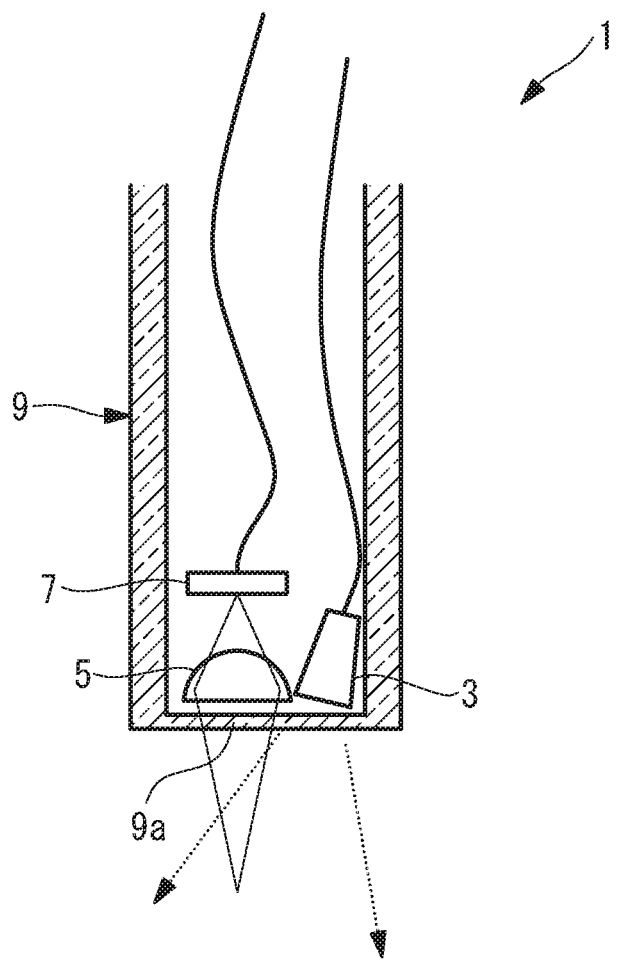
FIG. 3 is a longitudinal sectional view of the casing, showing an illumination unit, an image-forming optical system, and an imager in the casing.

As shown in FIG. 1, an observation device 1 of this embodiment is used to observe cells S that are cultured while being made to float in a culture fluid W inside a culture vessel 13. As shown in FIG. 3, the observation device 1 includes: an illumination unit 3 that generates illumination light to be radiated onto the cells S; an image-forming optical system 5 that images observation light coming from the cells S that have been irradiated with the illumination light by the illumination unit 3; an imager (light receiving unit) 7 that receives the observation light imaged by the image-forming optical system 5; and a casing 9 that accommodates the illumination unit 3, the image-forming optical system 5, and the imager 7.

The culture vessel 13 is a bottomed cylindrical vessel whose upper surface is closed, and accommodates the cells S together with the culture fluid W. The culture vessel 13 has, in the upper surface, a plurality of ports (tube ports) 13a via which various tubes 15 are inserted and an insertion port 13b via which a stirrer 17 is inserted.

In the example shown in FIG. 1, the three ports 13a are provided in the upper surface of the culture vessel 13, and the tubes 15 for collecting cells S in the culture fluid W and for administering a liquid medicine to the culture fluid W are inserted via the two ports 13a of the three ports 13a. An O-ring 19 (see FIG. 2) is provided on each of the ports 13a so as to close a gap with respect to the inserted tube 15.

The stirrer 17 includes a stir bar 17a that is inserted into the culture vessel 13 via the insertion port 13b of the culture vessel 13 and a stirring blade 17b that is provided at a distal end of the stir bar 17a. The stirrer 17 can stir the culture fluid W when the stir bar 17a and the stirring blade 17b are rotated about a longitudinal axis by a drive unit (not shown), such as a motor. Then, the culture fluid W is stirred by the stirrer 17, thereby preventing the cells S from sticking on an inner surface of the culture vessel 13 and making it possible to culture the cells S while making the cells S float in the culture fluid W.

Figure 2:
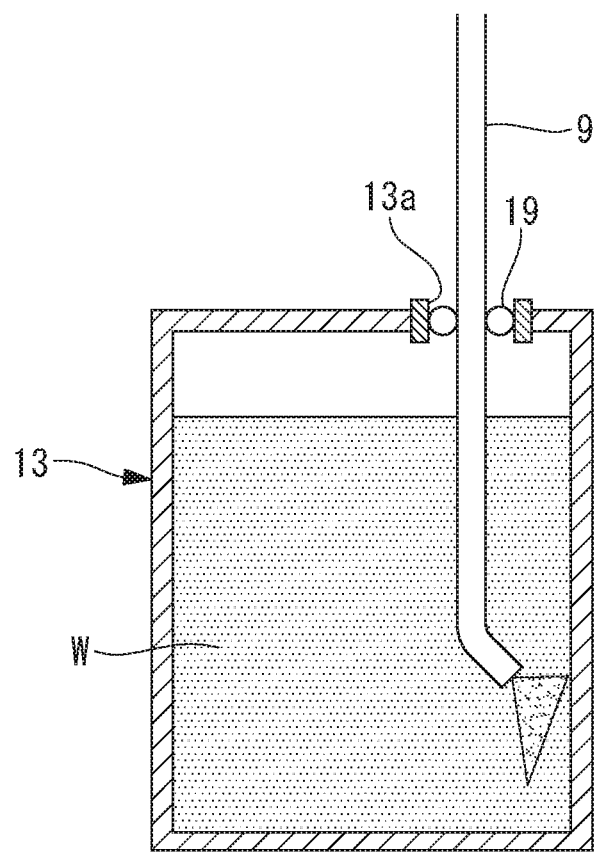
FIG. 2 is a longitudinal sectional view of the culture vessel, showing a longitudinal section of a port via which a casing shown in FIG. 1 is inserted.

The casing 9 has an elongated cylindrical form that can be inserted into the culture fluid W via the port 13a of the culture vessel 13. The casing 9 is made of, for example, polyvinyl chloride, and has flexibility. As shown in FIG. 2, for example, when the casing 9 is inserted via the port 13a, the gap between the port 13a and the casing 9 is closed by the O-ring 19, thus keeping the port 13a in a sealed state. Furthermore, as shown in FIG. 3, the casing 9 has, at a distal end thereof in the longitudinal direction, a transmissive section 9a that transmits illumination light and observation light.

The illumination unit 3 is, for example, an LED (Light-Emitting Diode). The illumination unit 3 is disposed at a distal-end section of the casing 9 so as to be opposed to the transmissive section 9a.

The image-forming optical system 5 is disposed at the distal-end section of the casing 9 so as to be opposed to the transmissive section 9a, side by side with the illumination unit 3. The image-forming optical system 5 images, on a light-receiving surface of the imager 7, observation light entering the casing 9 through the transmissive section 9a.

The imager 7 is, for example, a CCD (Charge-Coupled Device). The imager 7 is disposed in the distal-end section of the casing 9, at a position closer to the proximal end than the image-forming optical system 5 is. The imager 7 acquires an optical image of the received observation light, thereby outputting image information on the cells S.

As shown in FIG. 1, the observation device 1 includes an image processing unit 11.

Figure 4:
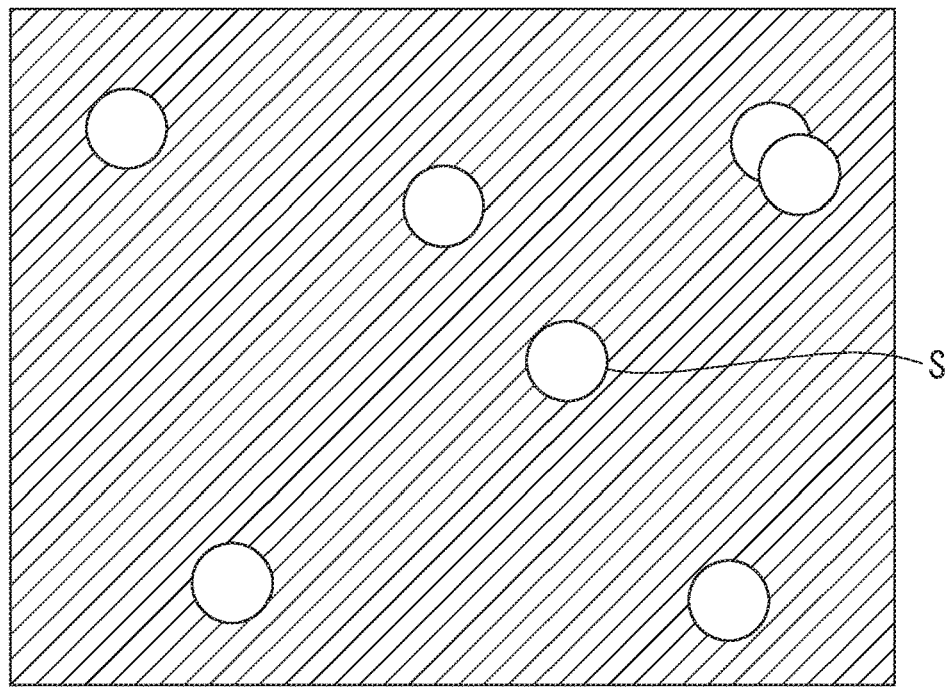
FIG. 4 is a view showing an example cell image generated by an image processing unit.

The image processing unit 11 processes an image signal output from the imager 7 and generates a two-dimensional cell image, such as that shown in FIG. 4. The image processing unit 11 counts the number of cells S included in the generated cell image. The image processing unit 11 estimates at least one of the number and the density of cells S in the culture fluid W, by using two or more cell images that are generated on the basis of observation light received by the imager 7 at times different from each other, i.e., two or more cell images that are acquired by the imager 7 at times different from each other.

In the two or more cell images used by the image processing unit 11, it is preferred that at least half of the cells S present in the images be changed, for example. More preferably, the image processing unit 11 may use two or more cell images that are generated on the basis of observation light received by the imager 7 at time intervals each longer than the duration of time from the appearance of the same cell S to the disappearance thereof in a cell image.

Figure 5:
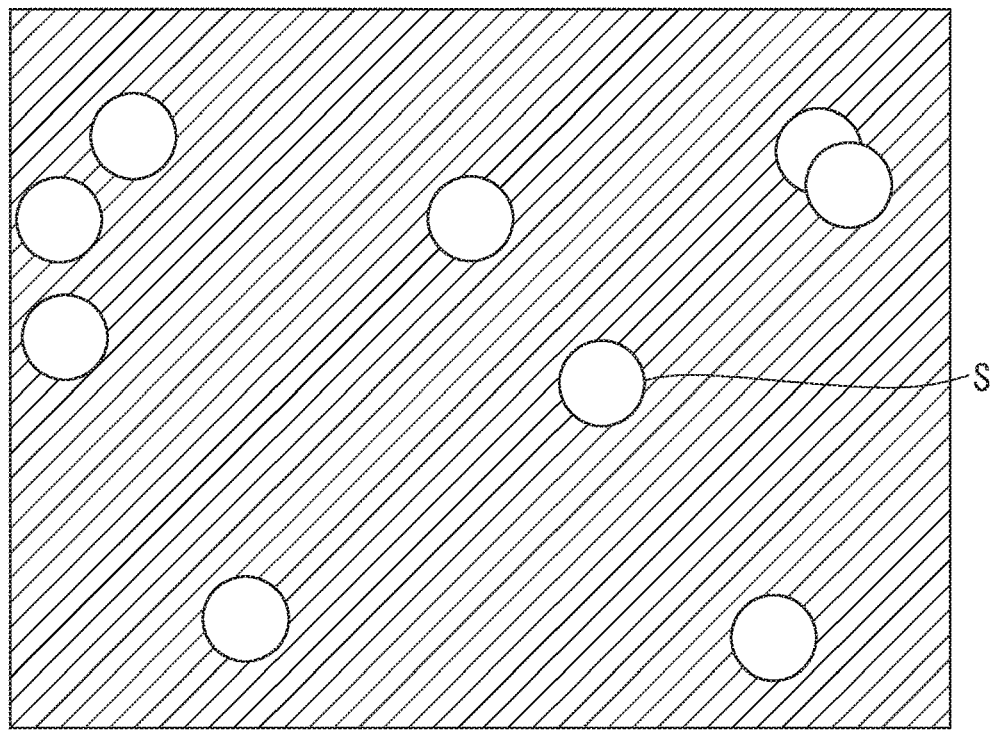
FIG. 5 is a view showing an example cell image acquired at a certain Time 1.
Figure 6:
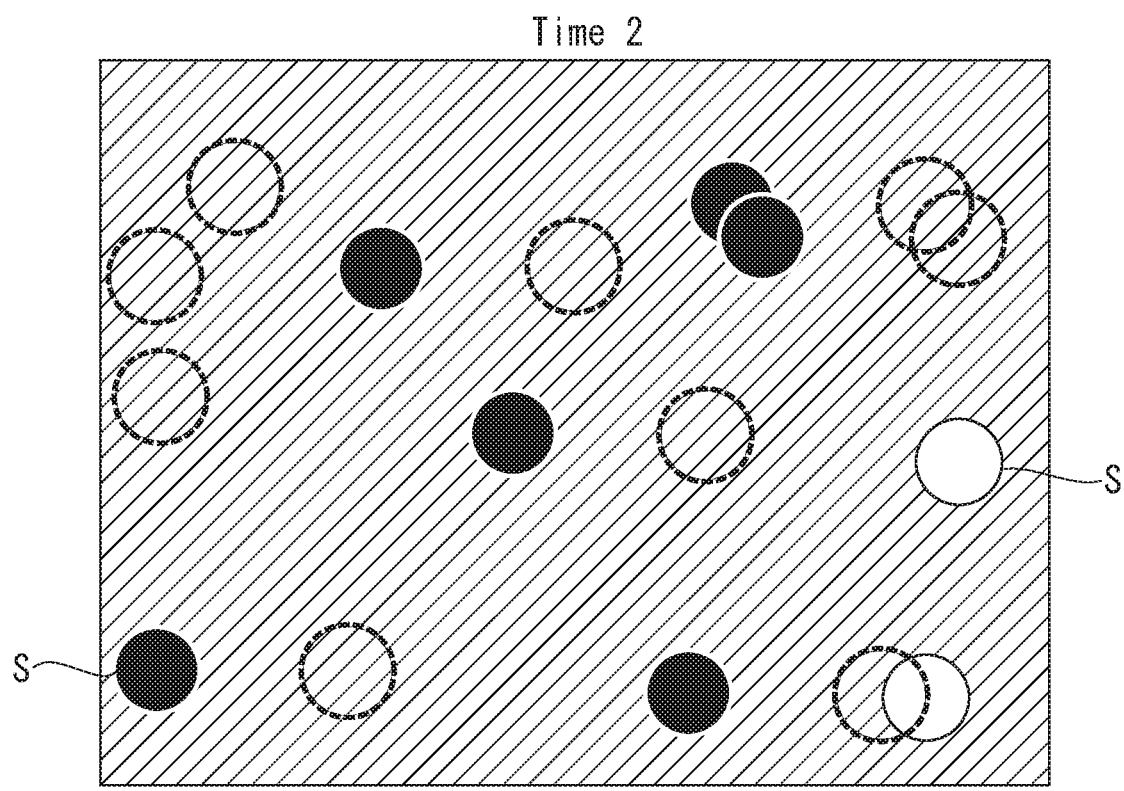
FIG. 6 is a view showing an example cell image acquired at Time 2 immediately after Time 1.

If the time interval at which cell images are acquired is too short, as shown in FIGS. 5 and 6, the same cells S are included in both cell images, thus making it impossible to accurately calculate the number and the density of cells S in the entire culture fluid W. In contrast to this, by using two or more cell images that are acquired by the imager 7 at time intervals each longer than the duration of time from the appearance of the same cell S to the disappearance thereof in a cell image, the image processing unit 11 can more accurately estimate the number and the density of cells S in the culture fluid W.

FIG. 5 shows a cell image acquired at certain Time 1, and FIG. 6 shows a cell image acquired at Time 2 immediately after Time 1. In FIGS. 5 and 6, white circles indicate cells S that are included in only one of the cell image at Time 1 and the cell image at Time 2. Black circles indicate cells S that are included in both the cell image at Time 1 and the cell image at Time 2. Circles drawn in broken lines indicate the positions where the cells S that are indicated by the black circles in the cell image at Time 2 were located at Time 1.

The operation of the observation device 1 of this embodiment will be described below.

In order to observe cells S that are cultured while being made to float in the culture fluid W inside the culture vessel 13, by using the observation device 1, which has the above-described configuration, first, as shown in FIG. 1, the casing 9 is inserted into the culture fluid W via the port 13a of the culture vessel 13. The casing 9 is sterilized in advance.

Next, the illumination unit 3 in the casing 9 radiates illumination light onto the cells S floating in the culture fluid W, through the transmissive section 9a of the casing 9. Observation light entering the casing 9 through the transmissive section 9a from the cells S irradiated with the illumination light is imaged by the image-forming optical system 5, and an optical image of the observation light is acquired by the imager 7.

Image information on the cells S acquired by the imager 7 is sent to the image processing unit 11, and the image processing unit 11 generates a two-dimensional cell image, such as that shown in FIG. 4, on the basis of the input image information. Accordingly, it is possible to acquire the image of the cells S floating in the culture fluid W. In the same way, the observation device 1 acquires a plurality of cell images at time intervals.

Next, the image processing unit 11 counts the number of cells S included in the generated cell images. The image processing unit 11 estimates the number and the density of cells S in the culture fluid by using two or more cell images generated on the basis of the image information on the cells S acquired by the imager 7 at times different from each other.

Figure 7:
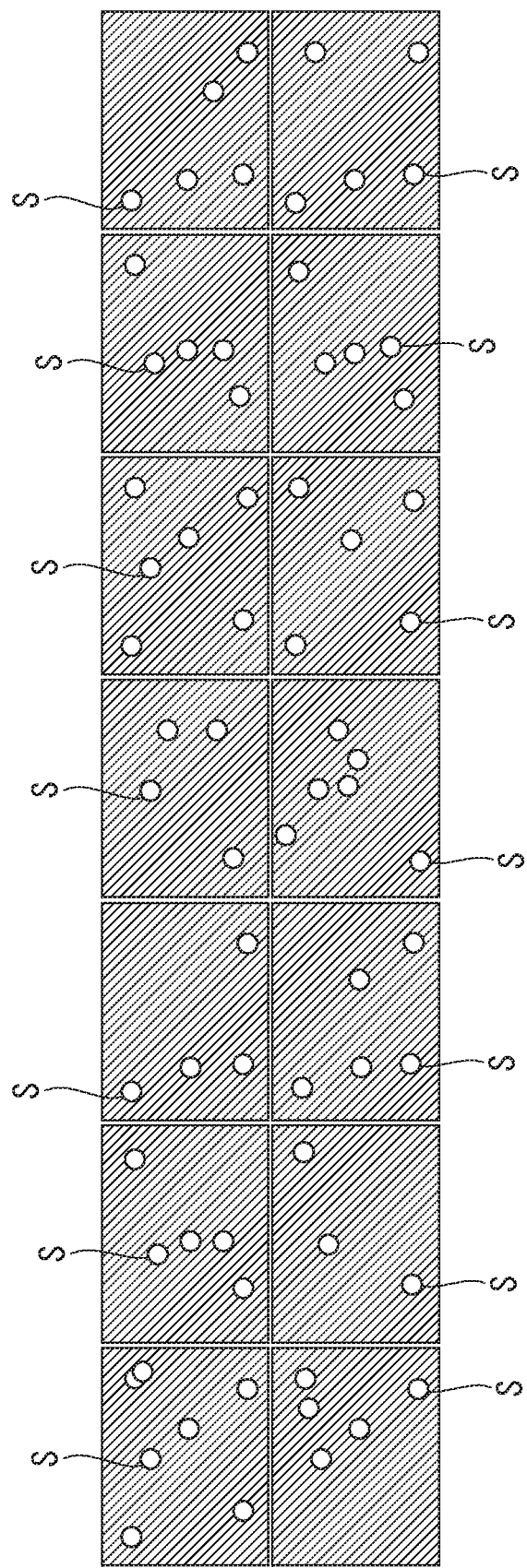
FIG. 7 is a view showing example 14 cell images acquired by the imager at times different from each other.
Figure 8:
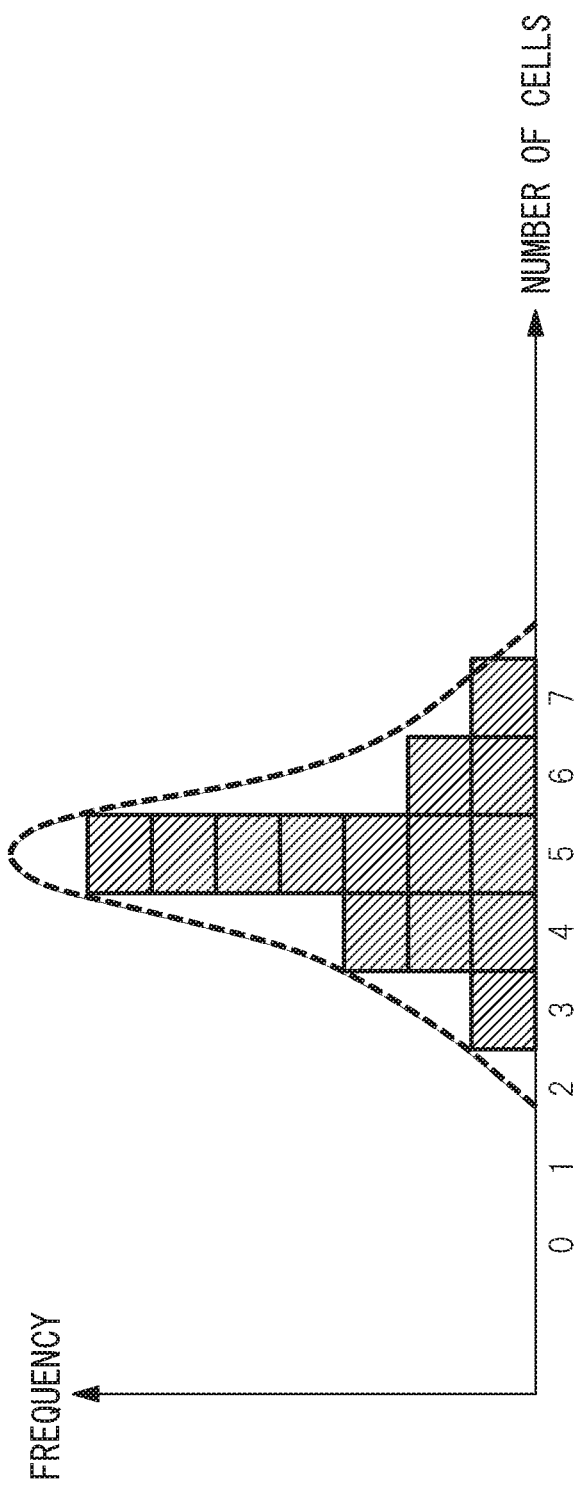
FIG. 8 is a graph showing an example relationship between the number of cells in a cell image and the frequency.

For example, as shown in FIG. 7, it is assumed that the imager 7 uses 14 cell images that are acquired at times different from one another. In this case, the image processing unit 11 calculates that the average number of cells is 4.92 cells, for example, as shown in FIG. 8. In FIG. 8, the horizontal axis shows the number of cells in each cell image, and the vertical axis shows the frequency. Furthermore, the image processing unit 11 calculates that, for example, the volume of an observation range is 1 mm×1 mm×0.1 mm=$10^{-4}$ cm$^3$=$10^{-4}$ ml, and the cell density is 4.92×$10^4$ cells/ml.

As described above, according to the observation device 1 of this embodiment, the casing 9 can be inserted into the culture vessel 13 by using one of the ports 13a, which are used to insert the tubes 15 into the culture vessel 13. Illumination light is radiated onto the cells S from the casing 9 inserted into the culture fluid W, and observation light from the cells S is received, thereby making it possible to acquire a good observation image of the cells S with almost no restrictions on the shape, the size, the material, etc. of the culture vessel 13 to be used. Therefore, it is possible to adapt to a great variety of culture vessels 13 and to stably observe the cells S in the culture fluid W inside the various culture vessels 13.

Figure 9:
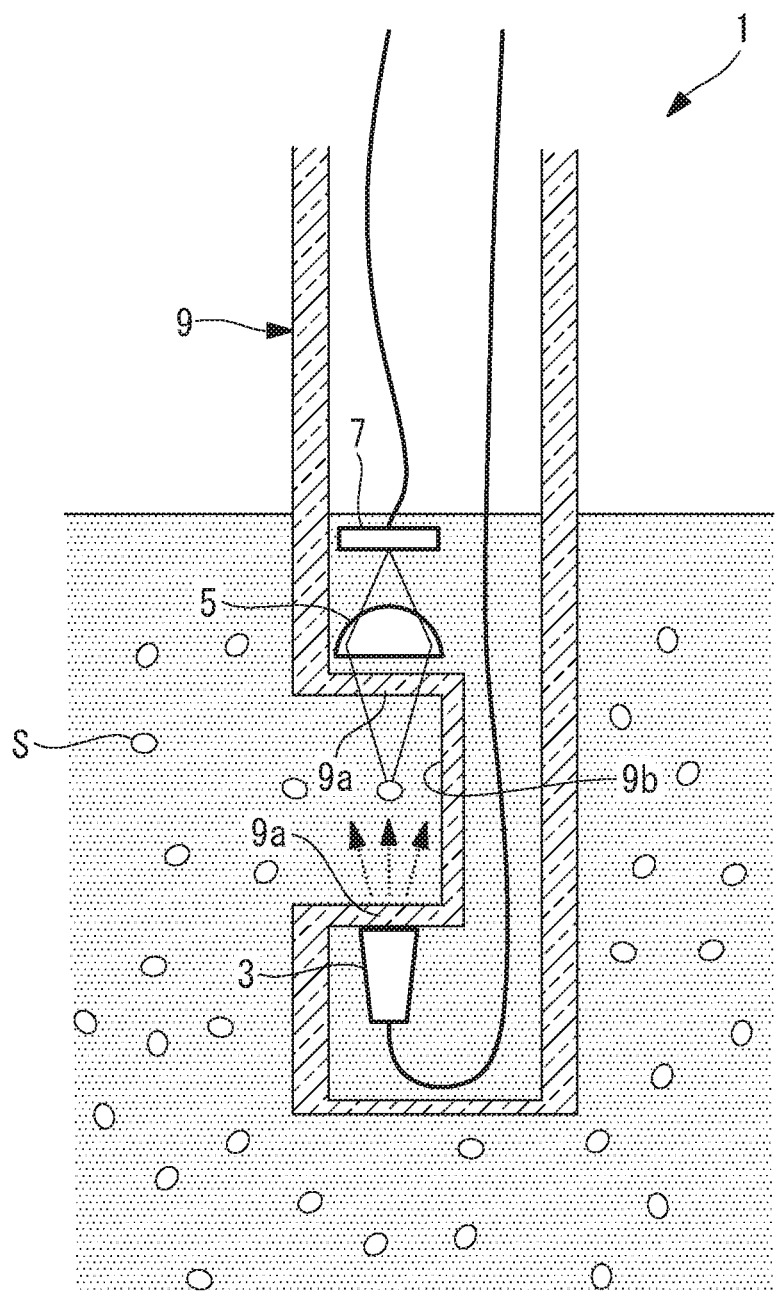
FIG. 9 is a longitudinal sectional view of the casing, showing an example casing according to a modification of the first embodiment of the present invention.

In this embodiment, for example, as shown in FIG. 9, the casing 9 may have, at a position closer to the proximal end than the distal end thereof in the longitudinal direction is, a recessed section 9b that is recessed radially inward, and transmissive sections 9a may be provided on both side surfaces of the recessed section 9b that are opposed to each other in the longitudinal direction of the casing 9.

In this case, in the casing 9, the illumination unit 3 is disposed in a space that is closer to the distal end than the recessed section 9b is so as to be opposed to one transmissive section 9a of the recessed section 9b. In the casing 9, the image-forming optical system 5 and the imager 7 are disposed in a space that is closer to the proximal end than the recessed section 9b is so as to be opposed to the other transmissive section 9a of the recessed section 9b.

With this configuration, the range to be irradiated with illumination light inside the culture vessel 13 is limited to the inside of the recessed section 9b, thereby making it possible to acquire an image of cells S that enter the inside of the recessed section 9b. Therefore, by limiting the image-acquisition range, it is easy to classify the sizes of the cells S in the cell image, and the volume of the image-acquisition range is made clear. Specifically, because the volume of the inside of the recessed section 9b is clear, it is possible to easily calculate the number and the density of the cells S.

Figure 10:
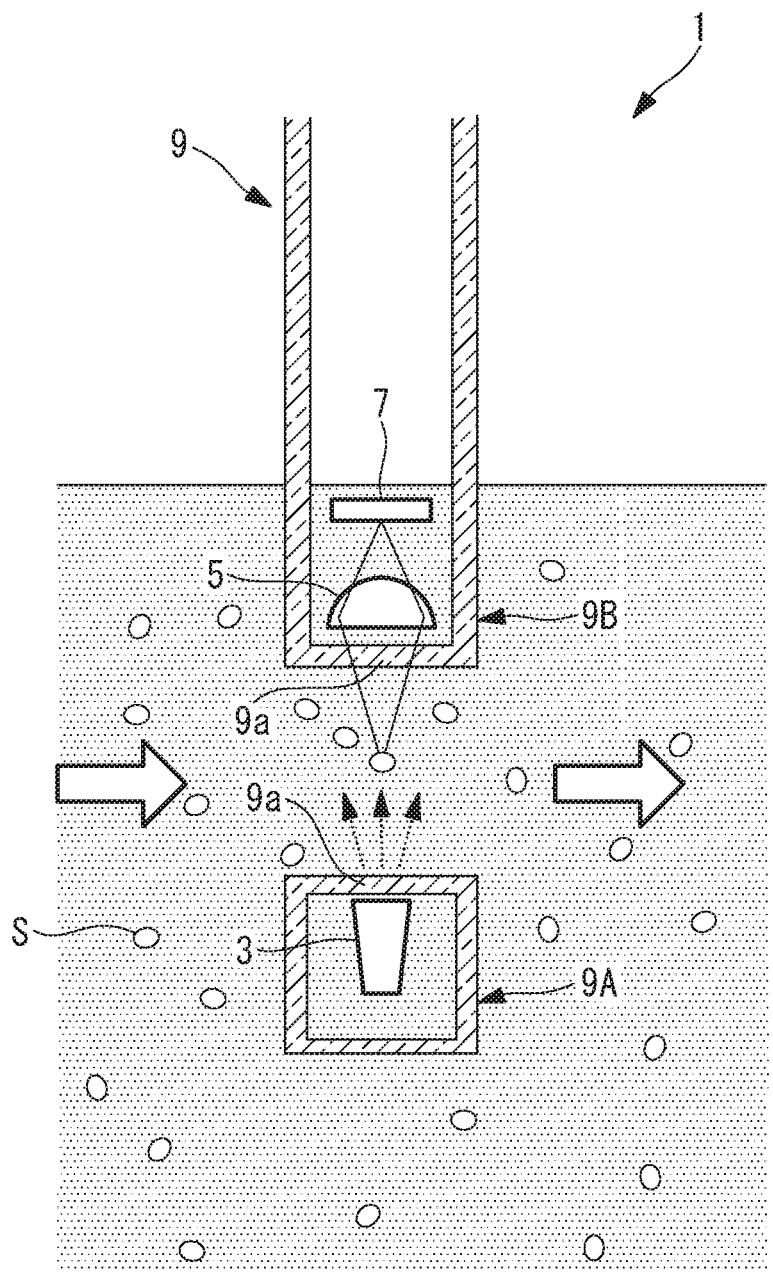
FIG. 10 is a longitudinal sectional view of the casing, showing another example casing according to a modification of the first embodiment of the present invention.

For example, as shown in FIG. 10, it is also possible to divide the casing 9 into a casing 9A that accommodates the illumination unit 3 and a casing 9B that accommodates the image-forming optical system 5 and the imager 7 and to dispose the casing 9A and the casing 9B at a distance from each other in the optical-axis direction of the illumination unit 3, the image-forming optical system 5, and the imager 7.

In this case, the illumination unit 3 in the casing 9A and the image-forming optical system 5 and the imager 7 in the casing 9B are disposed so as to be opposed to each other. The transmissive sections 9a are provided on the surfaces of the casing 9A and the casing 9B, the surfaces being opposed to each other.

With this configuration, the range to be irradiated with illumination light inside the culture vessel 13 is limited to the space between the casing 9A and the casing 9B, thereby making it possible to acquire an image of cells S that enter the space between the casing 9A and the casing 9B. In this case, by limiting the image-acquisition range, it is easy to classify the sizes of the cells S in the cell image, and the volume of the space between the casing 9A and the casing 9B is clear, thus making it easy to calculate the number and the density of the cells S.

Figure 11:
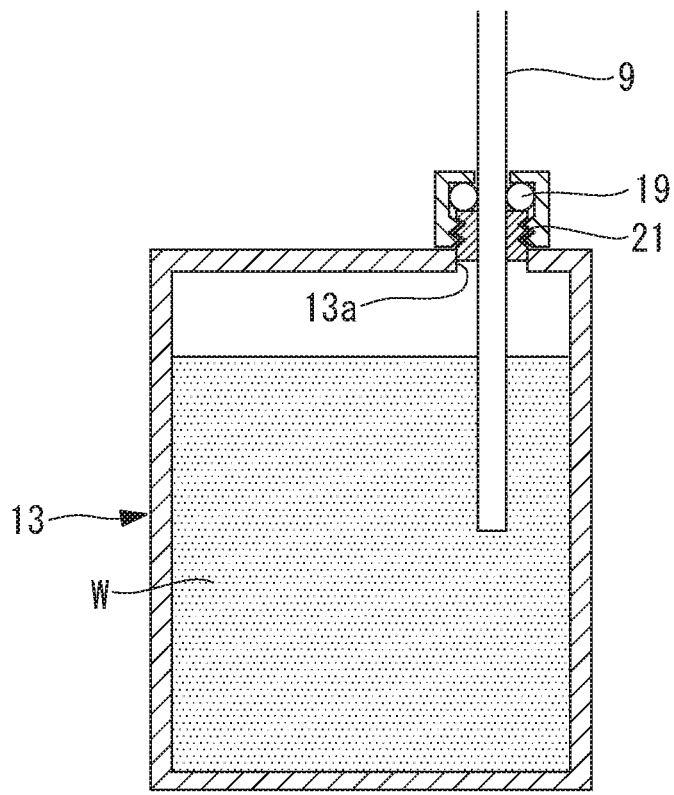
FIG. 11 is a longitudinal sectional view of the culture vessel, showing a longitudinal section of a port according to another modification of the first embodiment of the present invention.

In this embodiment, for example, as shown in FIG. 11, it is also possible to connect the port 13a and the O-ring 19 by using a substantially cylindrical bellows tube 21 that is expandable in the longitudinal direction. The bellows tube 21 may be formed of a material that can close the gap between the port 13a and the O-ring 19.

With this configuration, the bellows tube 21 allows the casing 9 to be moved in the insertion direction while maintaining the sealed state of the port 13a via which the casing 9 has been inserted. Instead of the bellows tube 21, an expandable elastic member may connect the port 13a and the O-ring 19 while closing the gap between the port 13a and the O-ring 19.

Second Embodiment

Next, an observation device according to a second embodiment of the present invention will be described below.

Figure 12:
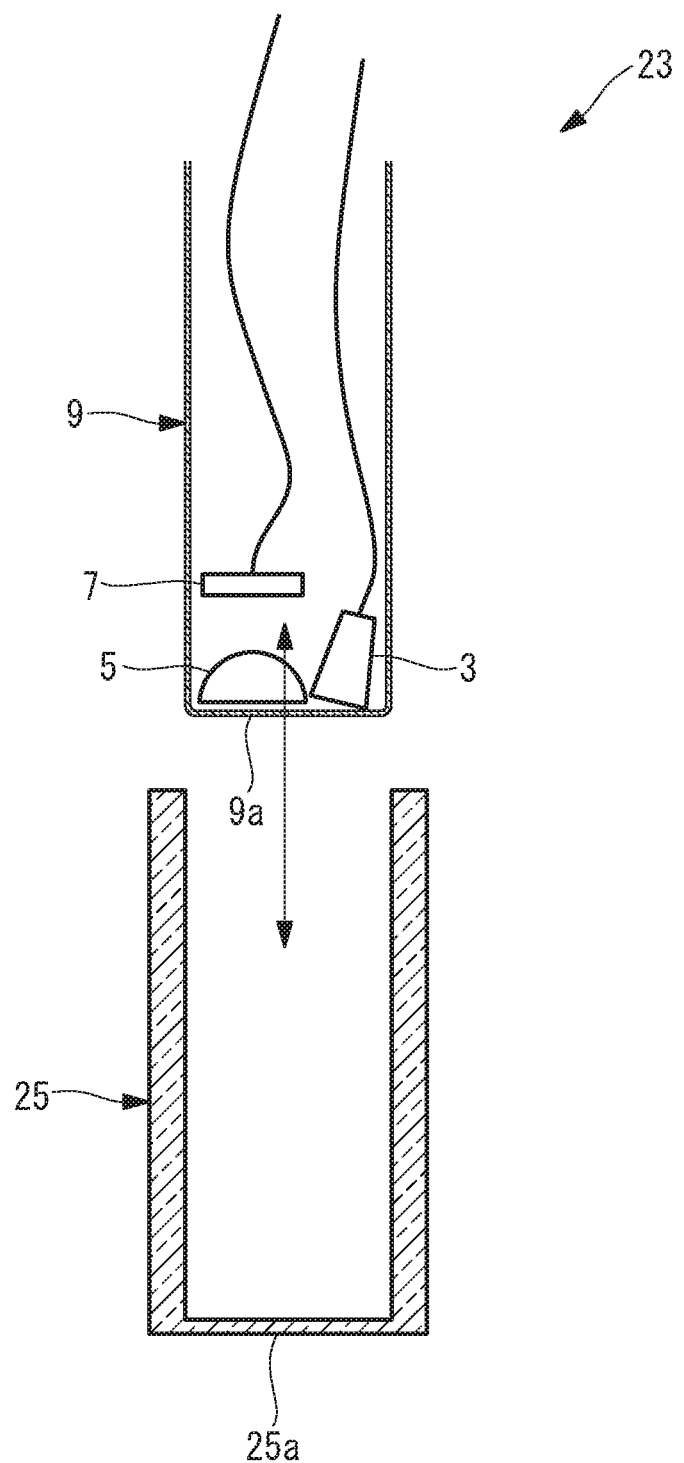
FIG. 12 is a schematic configuration view showing an observation device according to a second embodiment of the present invention.

As shown in FIG. 12, an observation device 23 of this embodiment differs from that of the first embodiment in that a cylindrical protective tube 25 that covers around the casing 9 is included.

Hereinafter, identical reference signs are assigned to components that have configurations common to those of the observation device 1 of the first embodiment, and a description thereof will be omitted.

The protective tube 25 has an elongated shape that can be inserted into the culture fluid W via the port 13a of the culture vessel 13. The protective tube 25 is formed so as to allow the casing 9 to be detachably inserted thereinto. The protective tube 25 is made of, for example, a transparent resin material, such as acrylic resin (PMMA) or polyvinyl chloride. Therefore, the whole of the protective tube 25 forms a transparent section that is optically transparent so as to transmit illumination light and observation light. In this embodiment, it is assumed that a distal end of the protective tube 25 in the longitudinal direction is a transparent section 25a.

According to the observation device 23 of this embodiment, with the protective tube 25 covering around the casing 9, the casing 9 is inserted into the culture fluid W via the port 13a of the culture vessel 13. Illumination light emitted by the illumination unit 3 is radiated onto the cells S through the transmissive section 9a of the casing 9 and the transparent section 25a of the protective tube 25, and observation light coming from the cells S through the transparent section 25a of the protective tube 25 and the transmissive section 9a of the casing 9 is formed into an image by the image-forming optical system 5. Accordingly, the formed image of the observation light is received by the imager 7, and a cell image is acquired.

In this case, the protective tube 25 has a shape that can be inserted into the culture fluid W via the port 13a of the culture vessel 13, thereby making it possible to insert the casing 9, the illumination unit 3, the image-forming optical system 5, and the imager 7 into the culture vessel 13 and to allow them to be operated inside the culture vessel 13, in a state in which the protective tube 25 safely protects the casing 9, and the illumination unit 3, the image-forming optical system 5, and the imager 7, which are accommodated in the casing 9. The protective tube 25 is made of a transparent resin material, such as acrylic resin or a polyvinyl chloride, thereby making it possible to use the protective tube 25 in a UV-sterilized state and to replace, after use, only the protective tube 25 so as to be disposable.

Figure 13:
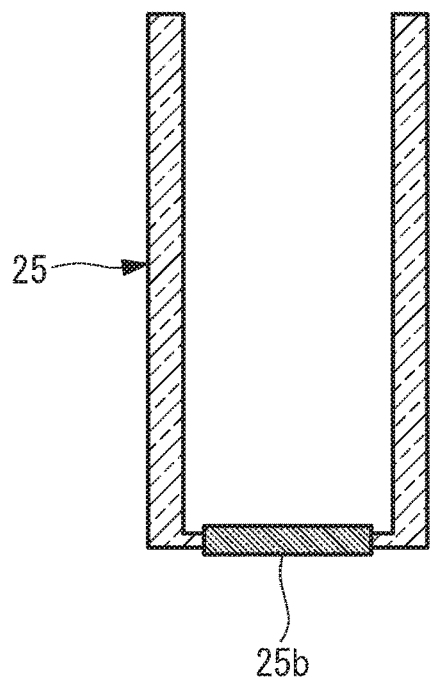
FIG. 13 is a longitudinal sectional view of a protective tube, showing an example protective tube according to a modification of the second embodiment of the present invention.

In this embodiment, although the protective tube 25 is made of a resin material, instead of this, for example, as shown in FIG. 13, the protective tube 25 may be a metal tube that is made of a metal material. In this case, optically transparent glass (transparent section) 25*b* is provided at the distal end of the protective tube 25. The protective tube 25 may have a bellows structure that is expandable in the longitudinal direction.

Figure 14:
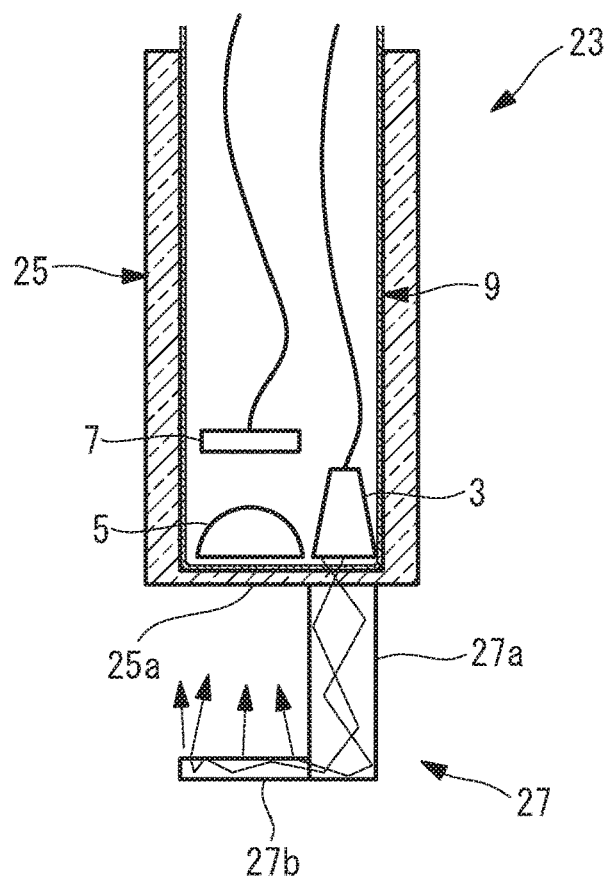
FIG. 14 is a longitudinal sectional view of the protective tube, showing a protrusion in one form according to another modification of the second embodiment of the present invention.
Figure 15:
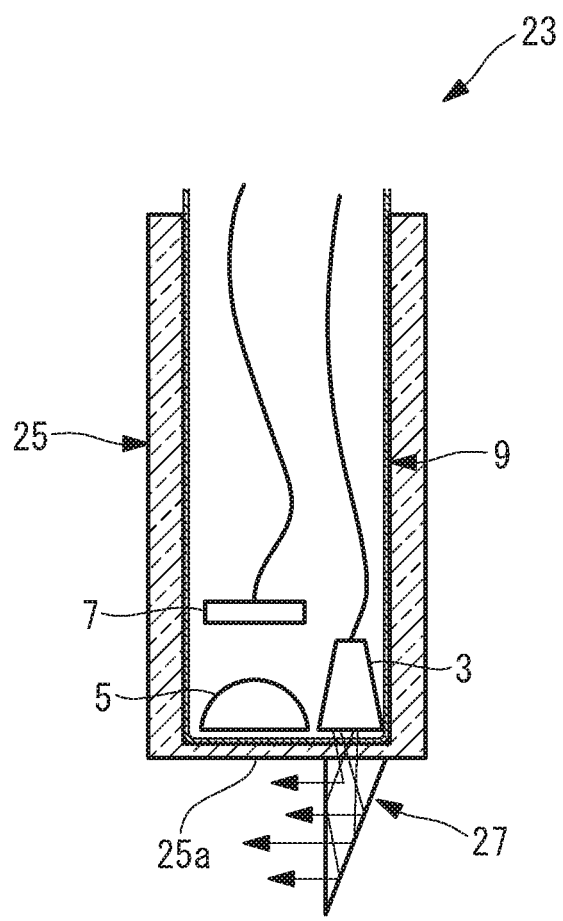
FIG. 15 is a longitudinal sectional view of the protective tube, showing a protrusion in another form according to still another modification of the second embodiment of the present invention.
Figure 16:
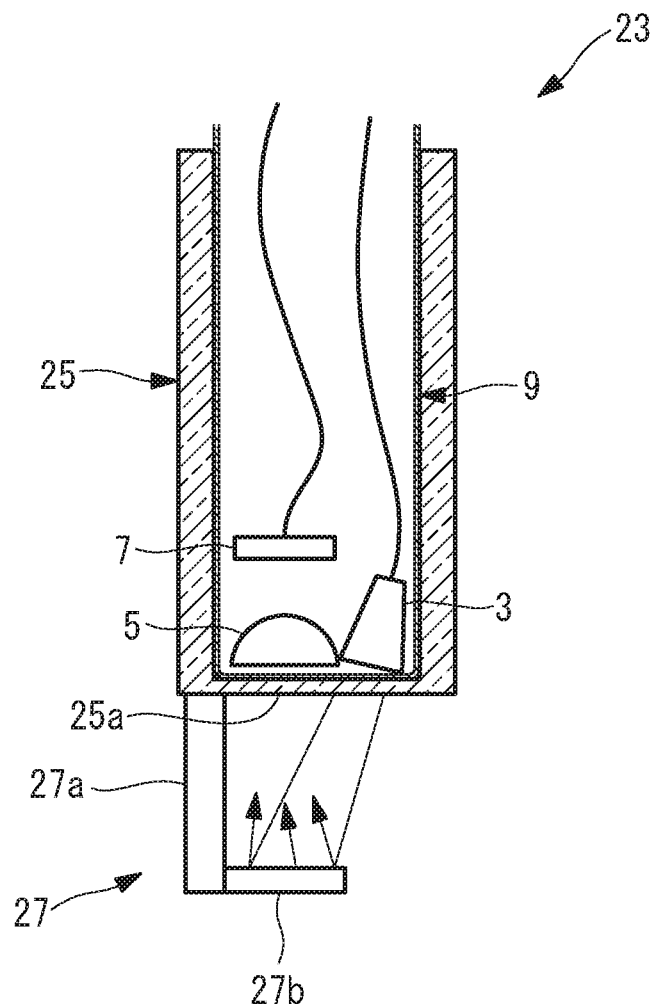
FIG. 16 is a longitudinal sectional view of the protective tube, showing a protrusion in still another form according to still another modification of the second embodiment of the present invention.

In this embodiment, for example, as shown in FIGS. 14 to 16, the protective tube 25 may have a protrusion (protruding part) 27 that protrudes outward from the transparent section 25*a*, and the protrusion 27 may transmit and/or reflect at least part of illumination light that has been transmitted through the transparent section 25*a*, toward the cells S. The protrusion 27 may be made of, for example, plastic.

As shown in FIG. 14, for example, the protrusion 27 may have: a pillar part 27*a* that extends from the distal end of the protective tube 25 along the longitudinal direction of the protective tube 25; and a bent part 27*b* that widens from a distal end of the pillar part 27*a* in parallel to the transparent section 25*a* of the protective tube 25. The pillar part 27*a* may be disposed on the optical axis of the illumination unit 3, and the bent part 27*b* may be disposed on the optical axis of the image-forming optical system 5.

In this case, illumination light emitted by the illumination unit 3 and transmitted through the transparent section 25*a* of the protective tube 25 is transmitted through the pillar part 27*a* of the protrusion 27 along the longitudinal direction, is then reflected along the shape of the protrusion 27, is transmitted through the bent part 27*b*, and is emitted, in front of the transparent section 25*a* of the protective tube 25, from the bent part 27*b* toward the transparent section 25*a* of the protective tube 25.

With this configuration, the range to be irradiated with illumination light inside the culture vessel 13 is limited to the space between the transparent section 25*a* of the protective tube 25 and the bent part 27*b* of the protrusion 27, thereby making it possible to acquire an image of cells S that enter the space between the transparent section 25*a* of the protective tube 25 and the bent part 27*b* of the protrusion 27.

Therefore, by limiting the image-acquisition range, it is easy to classify the sizes of the cells S in the cell image, and the volume of the image-acquisition range is made clear. Specifically, because the volume of the space between the transparent section 25*a* of the protective tube 25 and the bent part 27*b* of the protrusion 27 is clear, it is possible to easily calculate the number and the density of the cells S.

As shown in FIG. 15, for example, the protrusion 27 may have a conical or pyramid form that extends from the distal end of the protective tube 25 along the longitudinal direction and that gradually decreases in diameter. The protrusion 27 may be disposed on the optical axis of the illumination unit 3.

In this case, illumination light emitted by the illumination unit 3 and transmitted through the transparent section 25*a* of the protective tube 25 is reflected inside the protrusion 27 and is emitted from the protrusion 27 in the direction along the transparent section 25*a* of the protective tube 25. Accordingly, it is possible to radiate the illumination light onto the cells S in a direction intersecting the optical axis of the image-forming optical system 5, in the vicinity of the transparent section 25*a* of the protective tube 25. Observation light emitted from the cells S, which have been irradiated with the illumination light emitted from the protrusion 27, toward the transparent section 25*a* of the protective tube 25 is imaged by the image-forming optical system 5.

With this configuration, it is possible to acquire an image of cells S that are present in the space between the transparent section 25*a* of the protective tube 25 and the protrusion 27. Therefore, by limiting the image-acquisition range, it is easy to classify the sizes of the cells S in the cell image, and the volume of the image-acquisition range is made clear. Thus, it is possible to easily calculate the number and the density of the cells S. Compared with a case in which the protrusion 27 is not provided at the distal end of the protective tube 25, it is possible to change the way of adding contrast.

For example, as shown in FIG. 16, it is also possible to adopt the protrusion 27 that has the pillar part 27*a* and the bent part 27*b*, to dispose the pillar part 27*a* at a position shifted from the optical axis of the illumination unit 3 and the optical axis of the image-forming optical system 5, and to dispose the bent part 27*b* on the optical axes of the illumination unit 3 and the image-forming optical system 5, thereby forming a reflective surface.

In this case, illumination light emitted by the illumination unit 3 and transmitted through the transparent section 25*a* of the protective tube 25 is reflected at the bent part 27*b* of the protrusion 27 toward the transparent section 25*a* of the protective tube 25, in front of the transparent section 25*a* of the protective tube 25.

With this configuration, the range to be irradiated with illumination light inside the culture vessel 13 is limited to the space between the transparent section 25*a* of the protective tube 25 and the bent part 27*b* of the protrusion 27, thereby making it possible to acquire an image of cells S that enter the space between the transparent section 25*a* of the protective tube 25 and the bent part 27*b* of the protrusion 27.

Therefore, by limiting the image-acquisition range, it is easy to classify the sizes of the cells S in the cell image, and the volume of the space between the transparent section 25*a* of the protective tube 25 and the bent part 27*b* of the protrusion 27 is clear, thus making it possible to easily calculate the number and the density of the cells S.

Figure 17:
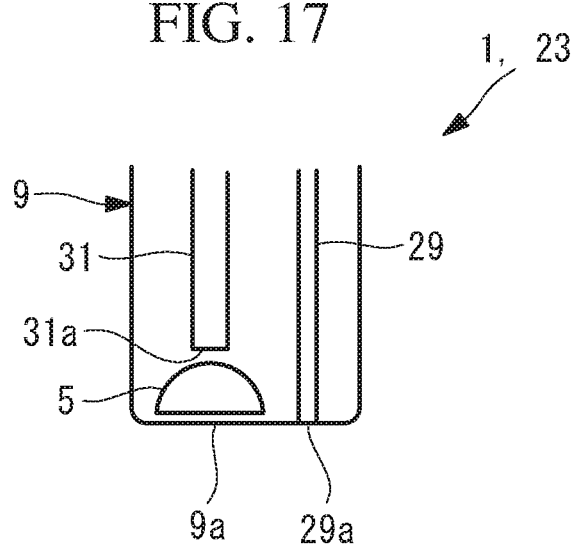
FIG. 17 is a longitudinal sectional view of the casing, showing an example fiber and bundle fiber according to a modification of the first embodiment and the second embodiment of the present invention.

In the above-described embodiment, although a description has been given of an example case in which the illumination unit 3, such as an LED, is shown as the illumination unit, for example, as shown in FIG. 17, the illumination unit 3 may further include a fiber 29 that guides light emitted by an LED (not shown) and that makes the light output from an output end 29*a* at the distal end thereof. In this case, the LED is disposed at the proximal end of the casing 9, and the output end 29*a* of the fiber 29 is disposed in the vicinity of the transmissive section 9*a* at the distal end of the casing 9. It is also possible to dispose the LED outside the proximal end of the casing 9 and to emit illumination light, through the fiber 29, to the transmissive section 9*a* at the distal end of the casing 9.

In the above-described embodiment, a description has been given of an example case in which the imager 7, such as a CCD, is shown as the light receiving unit; however, for example, as shown in FIG. 17, the light receiving unit may further include a bundle fiber 31 that receives light at an input end 31*a* and that guides the received light to a CCD or the like (not shown). In this case, the CCD or the like is disposed at the proximal end of the casing 9, and the input end 31*a* of the bundle fiber 31 is disposed in the vicinity of the image-forming optical system 5 at the distal-end section of the casing 9.

In this embodiment, for example, as shown in FIG. 18, the image-forming optical system 5 may be replaced with another image-forming optical system 5 in which at least one of the magnification, the depth of field, and the direction of the observation field of view is different. With this configuration, the optical field of view can be changed according to the image-forming optical system 5 to be used.

For example, in FIG. 18, the image-forming optical system 5 may be replaced with an image-forming optical system 5 that is shown at the left side in the figure, i.e., an image-forming optical system 5 with which the magnification is increased to allow image acquisition of a position close to the transmissive section 9a of the casing 9.

For example, in FIG. 18, the image-forming optical system 5 may be replaced with an image-forming optical system 5 that is shown at the center in the figure, i.e., an image-forming optical system 5 with which the focal length is increased to allow image acquisition of up to a position far from the transmissive section 9a of the casing 9.

For example, in FIG. 18, the image-forming optical system 5 may be replaced with an image-forming optical system 5 that is shown at the right side in the figure, i.e., an image-forming optical system 5 that is disposed so as to face a side surface of the casing 9 and that images observation light entering the casing 9 through the side surface. In this case, a prism 33 is disposed at the distal-end section of the casing 9, and the observation light focused by the image-forming optical system 5 is reflected at the prism 33 toward the bundle fiber 31. The illumination unit 3 is also disposed so as to face the side surface of the casing 9, and the transmissive section 9a is provided in the side surface of the casing 9, to which the illumination unit 3 and the image-forming optical system 5 are opposed. With this configuration, a region in a direction intersecting the depth direction of the culture vessel 13 can be observed without bending the distal-end section of the casing 9 in the culture vessel 13.

Although the embodiments of the present invention have been described above in detail with reference to the drawings, the specific configurations are not limited to these embodiments, and design changes that do not depart from the scope of the present invention are also encompassed. For example, the present invention is not limited to those applied to the above-described embodiments and modifications, can be applied to an embodiment obtained by appropriately combining the above-described embodiments and modifications, and is not particularly limited.

For example, although the imager 7, i.e., a CCD, is shown as an example of the light receiving unit, instead of this, a PMT (photomultiplier tube) may also be adopted. In the above-described embodiments, although the casing 9 has the transmissive section 9a at the distal end in the longitudinal direction, for example, the whole of the casing 9 may also be capable of transmitting illumination light and observation light. The positions at which the transmissive section 9a of the casing 9 and the transparent section 25a or 25b of the protective tube 25 are disposed can be appropriately changed according to the positions of the illumination unit 3, the image-forming optical system 5, and the imager 7.

The above-described embodiment also leads to the following aspects.

According to one aspect, the present invention provides an observation device for observing cells floating in a culture fluid inside a culture vessel, the observation device including: an illumination unit that generates illumination light to be radiated onto the cells; an image-forming optical system that images observation light coming from the cells that have been irradiated with the illumination light by the illumination unit; a light receiving unit that receives the observation light imaged by the image-forming optical system; and a casing that has a transmissive section so as to transmit the illumination light and the observation light and that accommodates the illumination unit, the image-forming optical system, and the light receiving unit, wherein the casing has an elongated cylindrical form that can be inserted into the culture fluid via a tube port used to insert a tube into the culture vessel.

According to this aspect, illumination light generated by the illumination unit in the casing is radiated onto cells floating in a culture fluid inside the culture vessel, through the transmissive section of the casing. Then, observation light entering the casing through the transmissive section from the cells that have been irradiated with the illumination light is imaged by the image-forming optical system, and the imaged observation light is received by the light receiving unit. Accordingly, it is possible to acquire an image of the cells floating in the culture fluid.

In this case, the casing can be inserted into the culture vessel by using the tube port, which is used to insert a tube into the culture vessel. Illumination light is radiated onto the cells from the casing inserted into the culture fluid, and observation light from the cells is received, thereby making it possible to acquire a good observation image of the cells with almost no restrictions on the shape, the size, the material, etc. of the culture vessel to be used. Therefore, it is possible to adapt to a great variety of culture vessels and to stably observe cells in a culture fluid, regardless of a culture vessel to be used.

The above-described aspect may further include a cylindrical protective tube that covers around the casing, wherein the protective tube has a transparent section, which is optically transparent, and has such an elongated shape as to be insertable into the culture fluid via the tube port.

With this configuration, in a state in which the protective tube covers around the casing, illumination light generated by the illumination unit is radiated onto the cells through the transparent section of the protective tube, and observation light from the cells is imaged by the image-forming optical system through the transparent section of the protective tube.

In this case, with the protective tube having a shape that can be inserted into a culture fluid via the tube port of the culture vessel, the casing, the illumination unit, the image-forming optical system, and the light receiving unit can be inserted into the culture vessel and can be operated in the culture vessel, in a state in which the protective tube safely protects the casing and the illumination unit, the image-forming optical system, and the light receiving unit, which are accommodated in the casing.

In the above-described aspect, the protective tube may be made of a transparent resin material.

With this configuration, it is possible to use the protective tube in a UV-sterilized state and to replace, after use, only the protective tube so as to be disposable.

In the above-described aspect, the protective tube may have a protruding part that protrudes outward from the transparent section, and the protruding part transmits and/or reflects, toward the cells, at least part of the illumination light that has been transmitted through the transparent section.

With this configuration, of illumination light that had been transmitted through the transmissive section of the protective tube, illumination light that has been transmitted through the protruding part and/or illumination light that has been reflected at the protruding part is radiated onto the cells in the culture fluid. Accordingly, the range to be irradiated with the illumination light inside the culture vessel is limited, thus making it possible to easily and accurately calculate the number and the density of cells. Compared with a case in which illumination light is not made to pass through the protruding part, it is possible to significantly change the way of adding contrast and the sizes of cells in a cell image.

The above-described aspect may further include an image processing unit that counts the number of the cells in a cell image generated on the basis of the observation light that has been received by the light receiving unit.

With this configuration, the number and the density of cells in the culture vessel can be estimated on the basis of the number of cells in a cell image, counted by the image processing unit.

In the above-described aspect, the image processing unit may estimate the number and/or the density of the cells in the culture fluid by using two or more cell images that have been generated on the basis of the observation light received by the light receiving unit at times different from each other.

Since the cells floating in the culture fluid move inside the culture vessel, when two or more cell images based on observation light received by the light receiving unit at times different from each other are used, the image processing unit can find an approximate number and/or density of cells in the culture fluid. Accordingly, it is possible to recognize an increase or decrease in the number of cells in the culture fluid.

In the above-described aspect, the two or more cell images may be generated on the basis of the observation light received by the light receiving unit at time intervals each longer than a duration of time from appearance of the same cell to disappearance thereof in each of the cell images.

If the time interval at which cell images are acquired is too short, the same cell is included in both cell images, thus making it impossible to accurately calculate the number and the density of cells in the entire culture fluid. By using two or more cell images based on observation light received by the light receiving unit at time intervals each longer than the duration of time from appearance of an identical cell to disappearance thereof in a cell image, the image processing unit can more accurately estimate the number and/or the density of cells in the culture fluid.

In the above-described aspect, the image-forming optical system may be replaceable with another image-forming optical system in which at least one of a magnification, a depth of field, and a direction of the observation field of view is different from the image-forming optical system.

With this configuration, the optical field of view can be easily changed according to the magnification, the depth of field, and the direction of the observation field of view of the other image-forming optical system to be used after replacement. Therefore, it is possible to acquire desired cell images according to an observation environment by changing the image-forming optical system.

REFERENCE SIGNS LIST 1, 23 observation device
3 illumination unit
5 image-forming optical system
7 imager (light receiving unit)
9 casing
9a transmissive section
11 image processing unit
13a port (tube port)
25 protective tube
25a, 25b transparent section
27 protrusion (protruding part)
29 fiber (illumination unit)
331 bundle fiber (light receiving unit)
S cell

The invention claimed is:

1. An observation device for observing cells floating in a culture fluid inside a culture vessel, the observation device comprising:
    an illumination unit comprising a light source configured to generate illumination light to be radiated onto the cells;
    a light receiving unit comprising an image sensor configured to receive observation light coming from the cells that have been irradiated with the illumination light, the observation light being imaged by an image-forming optical system; and
    a casing that has a transmissive section so as to transmit the illumination light and the observation light and that accommodates at least a portion of the illumination unit and at least a portion of the light receiving unit,
    wherein the casing has an elongated cylindrical form that is configured to be inserted into the culture fluid via a port used to insert a tube into the culture vessel.

2. The observation device according to claim 1, wherein the illumination unit comprises a fiber that guides light emitted by the light source and that makes the light output from a distal end of the casing, the light source being disposed inside the casing side or being disposed outside the casing.

3. The observation device according to claim 1, wherein the light receiving unit comprises a fiber, and
    the fiber is configured to guide the received observation light to the image sensor disposed inside the casing or disposed outside the casing.

4. The observation device according to claim 1, wherein the casing includes, at a position closer to a proximal end than a distal end thereof in a longitudinal direction is, a recessed section that is recessed radially inward, and
    the transmissive section is provided on each of both side surfaces of the recessed section that are opposed to each other in the longitudinal direction.

5. The observation device according to claim 1, wherein the casing is divided into a first casing that accommodates at least the portion of the illumination unit and a second casing that accommodates at least the portion of the light receiving unit,
    the first casing and the second casing are disposed at a distance from each other in an optical-axis direction, and
    the transmissive section is provided on each of surfaces of the first casing and the second casing, the surfaces being opposed to each other.

6. The observation device according to claim 1, further comprising a cylindrical protective tube that covers around the casing,
    wherein the protective tube has a transparent section, which is optically transparent, and has such an elongated shape as to be insertable into the culture fluid via the port.

7. The observation device according to claim 6, wherein the protective tube is made of a transparent resin material.

8. The observation device according to claim 6, wherein the protective tube has a protruding part that protrudes outward from the transparent section, and
    the protruding part transmits and/or reflects, toward the cells, at least part of the illumination light that has been transmitted through the transparent section.

9. The observation device according to claim 1, wherein the image-forming optical system is configured to provide at least one of a predetermined magnification, a predetermined depth of field, and a predetermined direction of the observation field of view.

10. The observation device according to claim 9, wherein the image-forming optical system is disposed so as to face a side surface of the casing, and
the image-forming optical system includes a prism that reflects the observation light entering the image-forming optical system through the side surface of the casing toward the light receiving unit.

11. The observation device according to claim 1, further comprising a processor comprising hardware, the processor being configured to count the number of the cells in a cell image generated on the basis of the observation light that has been received by the light receiving unit.

12. The observation device according to claim 11, wherein the processor is configured to estimate the number and/or the density of the cells in the culture fluid by using two or more cell images that have been generated on the basis of the observation light received by the light receiving unit at times different from each other.

13. The observation device according to claim 12, wherein the two or more cell images are generated on the basis of the observation light received by the light receiving unit at time intervals each longer than a duration of time from appearance of the same cell to disappearance thereof in each of the cell images.

* * * * *